United States Patent
Dunham et al.

(10) Patent No.: US 9,186,123 B1
(45) Date of Patent: Nov. 17, 2015

(54) ULTRASOUND SCANNERS WITH ANISOTROPIC HEAT DISTRIBUTORS FOR ULTRASOUND PROBE

(75) Inventors: Paul Dunham, Bothell, WA (US); Dustin Green, Carnation, WA (US); Thomas Houck, Bellevue, WA (US)

(73) Assignee: FUJIFILM SonoSite, Inc., Bothell, WA (US)

( * ) Notice: Subject to any disclaimer, the term of this patent is extended or adjusted under 35 U.S.C. 154(b) by 544 days.

(21) Appl. No.: 12/862,618

(22) Filed: Aug. 24, 2010

(51) Int. Cl.
*A61B 8/00* (2006.01)

(52) U.S. Cl.
CPC .. *A61B 8/00* (2013.01); *A61B 8/546* (2013.01)

(58) Field of Classification Search
CPC .................................. A61B 8/546; A61B 8/00
USPC ............. 136/203; 324/509; 374/31; 600/459; 73/865.9
See application file for complete search history.

(56) References Cited

U.S. PATENT DOCUMENTS

| | | | |
|---|---|---|---|
| 5,421,203 A | | 6/1995 | Graff et al. |
| 5,721,463 A | | 2/1998 | Snyder |
| 6,037,032 A | * | 3/2000 | Klett et al. .................... 428/71 |
| 6,217,530 B1 | | 4/2001 | Martin et al. |
| 6,859,984 B2 | * | 3/2005 | Dinet et al. ................ 29/25.35 |
| 6,905,466 B2 | | 6/2005 | Salgo et al. |
| 7,314,447 B2 | * | 1/2008 | Park et al. .................... 600/459 |
| 7,382,617 B2 | * | 6/2008 | Yu et al. ....................... 361/704 |
| 7,473,030 B2 | * | 1/2009 | Bruce et al. .................... 374/31 |
| 8,033,190 B2 | * | 10/2011 | Renken et al. ............... 73/866.1 |
| 2004/0002655 A1 | * | 1/2004 | Bolorforosh et al. ......... 600/459 |
| 2005/0075573 A1 | * | 4/2005 | Park et al. .................... 600/459 |
| 2007/0152674 A1 | * | 7/2007 | Hubbell ....................... 324/509 |
| 2007/0167803 A1 | * | 7/2007 | Kaminski et al. ............ 600/459 |
| 2007/0276248 A1 | * | 11/2007 | Saito et al. ................... 600/459 |
| 2008/0121263 A1 | * | 5/2008 | Schutte et al. ................ 136/203 |
| 2009/0069688 A1 | * | 3/2009 | Aono et al. .................. 600/459 |

FOREIGN PATENT DOCUMENTS

WO    WO 2007/086180    *    8/2007    .............. A61B 8/00

OTHER PUBLICATIONS

Wirtz et al. "Thermal Management Using "Dry" Phase Change Materials", Proc. Fifteenth IEEE Semiconductor Thermal Measurement and Management Symposium, Mar. 9-11, 1999, San Diego CA, IEEE, pp. 74-82.*

* cited by examiner

*Primary Examiner* — Unsu Jung
*Assistant Examiner* — Serkan Akar
(74) *Attorney, Agent, or Firm* — Perkins Coie LLP

(57) ABSTRACT

Ultrasound scanners with anisotropic heat distributors and associated methods of operation are disclosed herein. In one embodiment, an ultrasound scanner can include a housing having a surface enclosing an internal cavity, an electronic component in the internal cavity of the housing, and a heat distributor between the surface of the housing and the electronic component. The heat distributor is in thermal communication with both the electronic component and the surface of the housing. The heat distributor includes a laminated structure having a conductive layer and a insulative layer stacked one on the other.

13 Claims, 12 Drawing Sheets

ULTRASOUND SCANNERS WITH ANISOTROPIC HEAT DISTRIBUTORS FOR ULTRASOUND PROBE

TECHNICAL FIELD

The present application is generally related to ultrasound scanners with anisotropic heat distributors, and associated methods of manufacturing and operating such ultrasound scanners.

BACKGROUND

Ultrasound imaging systems are widely used today in medicine for visualizing and diagnosing a variety of conditions. For example, ultrasound imaging systems can be used to visualize tendons, muscles, joints, vessels, internal organs, and/or other subcutaneous body structures for detecting possible pathology or lesions. Ultrasound imaging systems are also used in obstetrics to visualize an embryo or a fetus in a mother's uterus.

Ultrasound imaging systems typically include a processing station (e.g., a computer) linked to an ultrasound scanner. During scanning, the ultrasound scanner transmits sound waves into a body structure and detects echoes from the body structure. The ultrasound scanner then transmits data representing the detected echoes to the processing station, in which images of the scanned body structure can be formed, manipulated, and displayed.

Ultrasound scanners may, for example, include an array of separate transducer elements linked independently to the processing station by individual communication wires in a cable. As the number of the transducer elements increases (e.g., for improving image resolution), the number of communication wires in the cable also increases. Such large cables, however, are less flexible than smaller cables and are thus more cumbersome to operate. As a result, cables for high resolution devices with a large number of wires may not be flexible enough to allow ready operation of the ultrasound scanner.

DETAILED DESCRIPTION

The present technology is directed to ultrasound systems with ultrasound scanners having anisotropic heat distributors, and associated methods of manufacture and operation. As used herein, the term "ultrasound transducer array" generally refers to an array that can (1) generate and transmit sound waves and (2) receive and evaluate echoes in response to the transmitted sound waves. Ultrasound transducer arrays can be constructed from quartz, gallium orthophosphate, lithium niobate, lithium tantalite, sodium tungstate, and/or other suitable piezoelectric or non-piezoelectric materials. It will be appreciated that several of the details set forth below are provided to describe the following embodiments in a manner sufficient to enable a person skilled in the relevant art to make and use the disclosed embodiments. Several of the details described below, however, may not be necessary to practice certain embodiments of the technology. Additionally, the technology can include other embodiments that are within the scope of the claims but are not described in detail with respect to FIGS. 1A-4E.

Figure 1A:
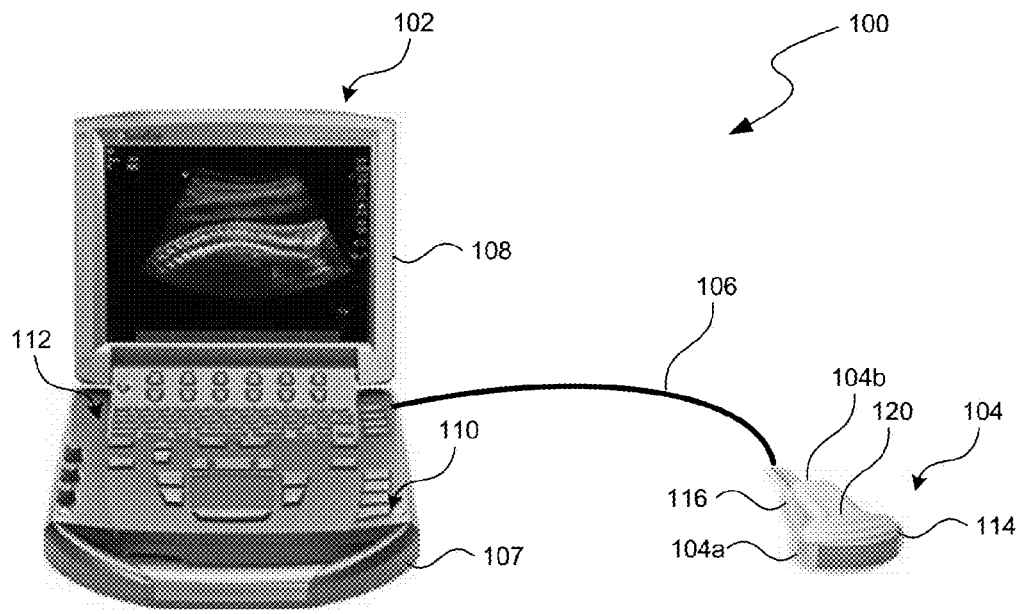
FIG. 1A is a perspective view of an ultrasound imaging system in accordance with embodiments of the technology.
Figure 1B:
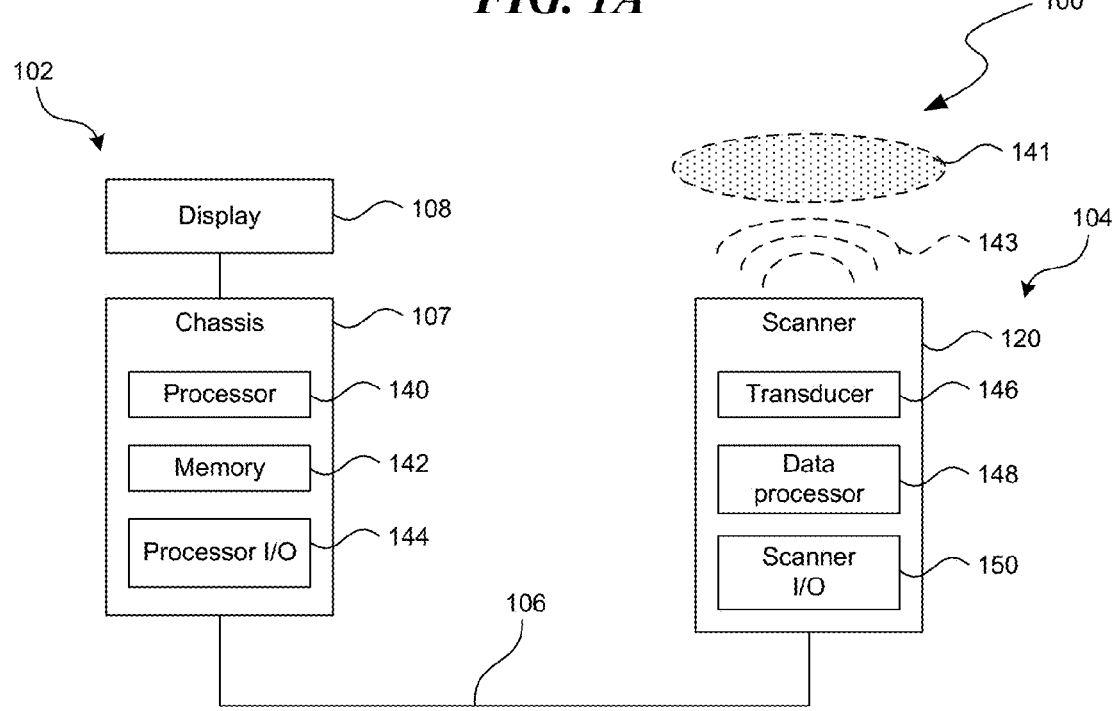
FIG. 1B is a schematic logic diagram of the ultrasound imaging system in FIG. 1A.

FIG. 1A is a perspective view and FIG. 1B is a schematic logic diagram of an ultrasound imaging system 100 in accordance with embodiments of the technology. As shown in FIG. 1A, the ultrasound imaging system 100 can include a processing station 102 coupled to an ultrasound scanner 104 with a communication link 106. In one embodiment, the communication link 106 includes a coaxial or other type of hardwire cable. In other embodiments, the communication link 106 can include a wireless link, an internet link, an intranet link, and/or other suitable communication connection.

As shown in FIG. 1A, the processing station 102 is configured as a mobile device and includes a chassis 107 operatively coupled to a display 108. The chassis 107 can carry one or more buttons 110, a keyboard 112, and/or other suitable input/output components. The display 108 can include a liquid crystal display, a plasma display, and/or another suitable graphic display. In other embodiments, the processing station 102 can also be configured as a handheld device, a cart-mounted device, a fixed-mounted device, or another suitable type of device.

The ultrasound scanner 104 can include a housing 120 with a scan head 114 at a distal end 104a and a hand grip 116 at a proximal end 104b. In the illustrated embodiment, the scan head 114 and the hand grip 116 of the ultrasound scanner 104 form a generally "T" shape. In other embodiments, the scan head 114 and the hand grip 116 can have other suitable geometric configurations based on particular applications. As described in more detail below with reference to FIG. 1B, the ultrasound scanner 104 can further include an ultrasound transducer array at the distal end 104a, electronic data processing components in the housing 120, at least one anisotropic heat distributor associated with housing 120 and the electronic data components, and/or other suitable mechanical or electrical components (not shown in FIG. 1A) in the housing 120.

As shown in FIG. 1B, the processing station 102 can include a logic processor 140, a memory 142 operatively coupled to the processor 140, and a processor input/output component 144. The logic processor 140 can include a microprocessor, a field-programmable gate array, and/or other suitable logic devices. The memory 142 can include volatile and/or nonvolatile computer storage media (e.g., ROM, RAM, magnetic disk storage media, optical storage media, flash memory devices, and/or other suitable computer readable media) configured to store data received from, as well as instructions for, the logic processor 140. The processor input/output component 144 can include device drivers configured to accept input from and provide output to an operator via the keyboard 112 (FIG. 1A), the buttons 110 (FIG. 1A), the display 108, and/or other suitable interfacing components of the processing station 102.

In the embodiment shown in FIG. 1B, the ultrasound scanner 104 includes an ultrasound transducer array 146, a data processor 148, and a scanner input/output component 150 operatively coupled to one another within the housing 120. The transducer array 146 can include an array of individual piezoelectric transducer elements (e.g., 256 lead zirconate titanate elements) and/or other suitable transducer elements. The data processor 148 can include analog/digital ("A/D") converters, band pass filters, rectifiers, and/or other suitable data processing components that digitize all of the echo data from the individual piezoelectric transducer elements of the transducer array 146 within the housing 120. The scanner input/output component 150 can include device drivers, transceivers, and/or other suitable components for sending data and receiving instructions to/from the processing station 102. In other embodiments, the ultrasound scanner 104 can also include a radio transceiver, data storage, and/or other suitable mechanical or electrical components (not shown) in the housing 120.

Referring to both FIGS. 1A and 1B, in operation, an operator (not shown) holds the ultrasound scanner 104 by the hand grip 116 and places the distal end 104a of the ultrasound scanner 104 proximate to or in contact with a structure to be examined, for example, a body structure 141 of a patient (shown in phantom lines for clarity). The ultrasound transducer array 146 then transmits sound waves 143 into the body structure 141 and detects echoes returning from the body structure 141. The ultrasound transducer array 146 can then convert the detected echoes into electrical signals representing the detected echoes.

The data processor 148 in the ultrasound scanner 104 receives the electrical signals representing the detected echoes from the ultrasound transducer array 146 and processes the echo signals to generate data representing the detected echoes of all of the individual transducer elements within the housing 120 of the ultrasound scanner 104. In one embodiment, the data processor 148 can digitize the echo signals into a collection of digital data. In another embodiment, the data processor 148 can digitize and compress the electrical signals in order to reduce the signals to a required bandwidth for transmitting the digitized data. In other embodiments, the data processor 148 can also apply various data compression, optimization and multiplexing techniques, such as for example, time division, code division, and/or otherwise manipulate the digitized data. The data processor 148 can then transmit the generated data to the processing station 102 via the communication link 106.

Several embodiments of the ultrasound scanner 104 do not require a separate wire in the communication link 106 for each separate transducer element. Unlike conventional ultrasound scanners, several embodiments of the ultrasound scanner 104 can digitize and/or otherwise process the electrical signals representing the detected echoes from all of the separate transducer elements such that the digitized data can be transmitted via fewer coaxial cables (or wireless channels) than the number of separate transducer elements. For example, all of the data from 256 separate transducer elements can be transmitted independently via one coaxial cable, one wireless channel, and/or another suitable single communication channel.

One challenge of processing the data within the housing 120 of the ultrasound scanner 104 in the foregoing fashion is that the data processor 148 can produce a large amount of heat in a short period of time. As a result, localized high-temperature areas ("hot spots") can occur rather quickly on the surface of the housing 120 at areas superimposed or otherwise juxtaposed to the data processor 148. The heat generated by the data processor 148 can be uncomfortable, and thus regulations have been published to limit the rate of temperature increase at the surface of the housing 120. To meet these regulations, several embodiments of the ultrasound scanner 104 can include a heat distributor configured to (1) preferentially conduct heat in one or more desired directions in the ultrasound scanner 104 to reduce hot spots on the surface of the housing 120 and (2) reduce the rate of temperature increase at the surface of the housing 120 to an acceptable level, as described in more detail below with reference to FIGS. 2A and 2E.

Figure 2A:
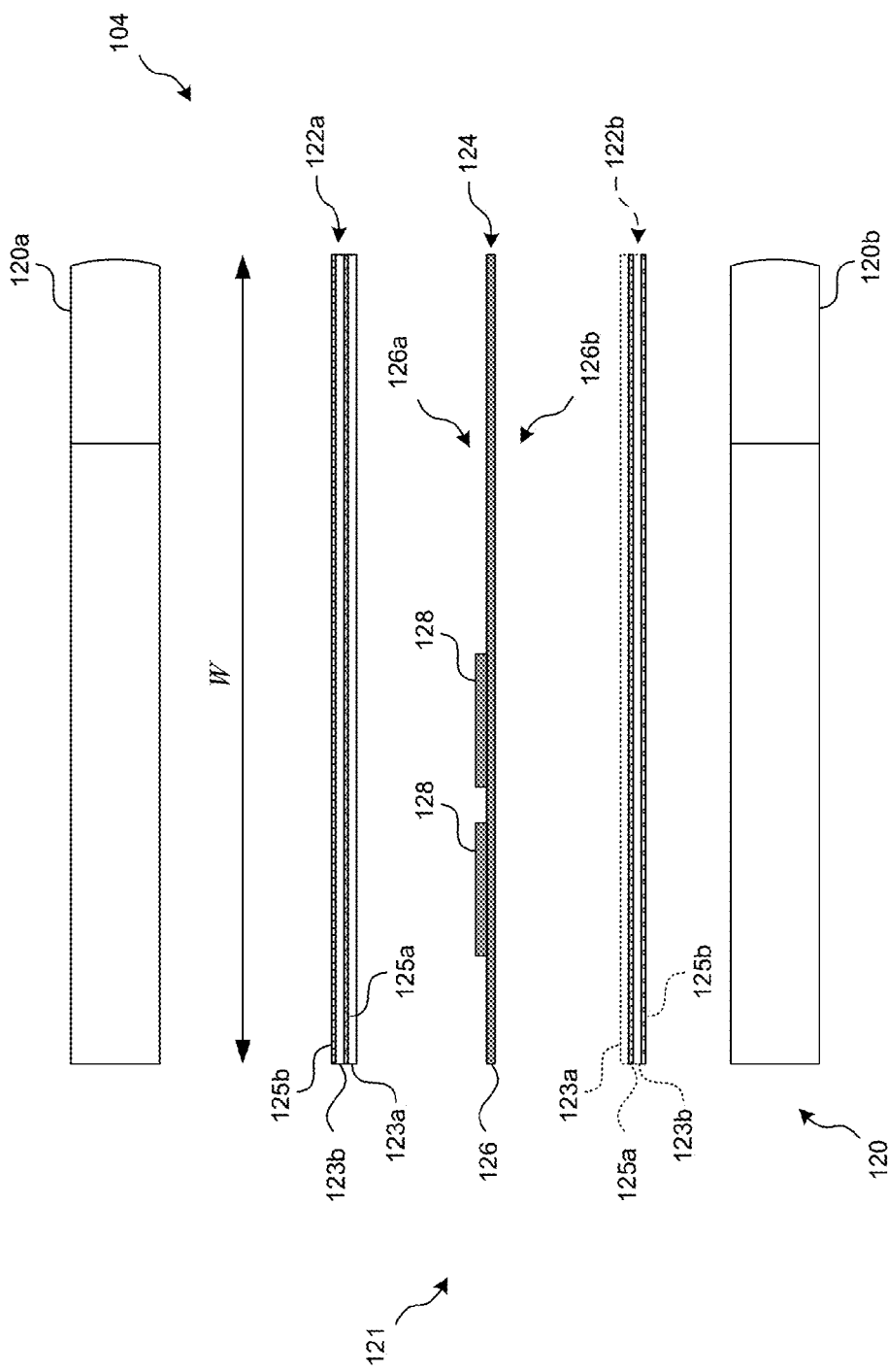
FIG. 2A is an exploded cross-sectional view of an ultrasound scanner suitable for use in the ultrasound imaging system in FIG. 1A in accordance with embodiments of the technology.

FIG. 2A is an exploded cross-sectional view of the ultrasound scanner 104 having one or more heat distributors in accordance with embodiments of the technology. As shown in FIG. 2A, the ultrasound scanner 104 can include a first housing portion 120a, a first heat distributor 122a, an electronic component 124, an optional second heat distributor 122b, and a second housing portion 120b arranged in series. In the illustrated embodiment, the second heat distributor 122b is generally similar in structure and function to the first heat distributor 122a. In other embodiments, the second heat distributor 122b can have different structures and/or functions than the first heat distributor 122a. In further embodiments, the second heat distributor 122b may be omitted, or additional heat distributors (not shown) can be incorporated into the ultrasound transducer 104.

In the illustrated embodiment, the first and second housing portions 120a and 120b are configured to mate vertically with each other to form an internal space 121 or cavity within the housing 120. The first and second housing portions 120a and 120b may be fastened together with an adhesive, a screw, snap-lock fittings, and/or other suitable fasteners. In other embodiments, the first and second housing portions 120a and 120b may also mate longitudinally to form the internal space 121 within the housing 120. In further embodiments, the first and second housing portions 120a and 120b may be formed as a unitary piece and/or have other suitable configurations.

The electronic component 124 can include a substrate 126 (e.g., a printed circuit board and/or other suitable substrate structures) and one or more semiconductor devices 128 mounted to the substrate 126. The semiconductor devices 128 can include A/D converters, memory devices, logic processors, and/or other suitable electronic components of the data processor 148 (FIG. 1B). In the illustrated embodiment, the semiconductor devices 128 are arranged on a first side 126a of the substrate 126. In other embodiments, the electronic component 124 can also include semiconductor devices (not shown) and/or other suitable electrical components on a second side 126b of the substrate 126 in addition to or in lieu of the semiconductor devices 128 on the first side 126a of the substrate 126. In further embodiments, the electronic component 124 can include more than one substrate 126 and/or can have other desired configurations.

The first heat distributor 122a can include a plurality of conductive layers 123 (identified individually as first and second conductive layers 123a and 123b) and a plurality of insulative layers 125 (identified individually as first and second insulative layers 125a and 125b) alternately stacked on one another. In certain embodiments, the conductive layers 123 and the insulative layers 125 can be laminated together with an adhesive and/or a fastener (not shown). In other embodiments, the conductive layers 123 and the insulative layers 125 can simply contact one another without any adhesive or fasteners.

In the illustrated embodiment, both the conductive layers 123 and the insulative layers 125 have the same width W. In other embodiments, the conductive layers 123 and the insulative layers 125 may have different widths, thicknesses, and/or other structural features. Even though only two conductive layers 123 and two insulative layers 125 are shown in FIG. 2A, it is understood that the first heat distributor 122a can include only one conductive layer 123 and/or insulative layer 125, or any desired number of conductive layers 123 and/or insulative layers 125.

In certain embodiments, the conductive layers 123 can be generally identical to one another, and/or the insulative layers 125 can be generally identical to one another. In other embodiments, one or more of the conductive layers 123 and/or the insulative layers 125 may be different than the others by individually including different materials, dimensions, structural features, and/or other suitable characteristics. For example, the first conductive layer 123a may have a first thickness that is different than a second thickness of the second conductive layer 123b. In another example, the first and second conductive layers 123a and 123b can include voids or different structural features, as described in more detail below with reference to FIG. 2E.

The conductive layers 123 can individually include a sheet, plate, slab, foil, and/or other suitable structure constructed from a metal (e.g., copper or aluminum), a metal alloy (e.g., stainless steel), and/or other suitable thermally conductive materials. The conductive layers 123, for example, can be configured to have a thermal conductivity greater than about 10 W/(m·K). In several embodiments, the conductive layers 123 can be solid structures. In other embodiments, the conductive layers 123 can include apertures, openings, slots, channels, and/or other suitable structural features, as described in more detail below with reference to FIG. 2E.

The insulative layers 125 can individually include a sheet, plate, slab, and/or other suitable structure constructed from a material with a low thermal conductivity. For example, in certain embodiments, the insulative layers 125 can individually include a layer of cotton, clay, epoxy, fiberglass, foam, matrix, and/or other materials with a thermal conductivity less than about 10 W/(m·K). In other embodiments, the insulative layers 125 can also be made of a composite material embedded with or otherwise carrying a phase change material ("PCM") that can absorb heat and maintain a generally constant temperature for a period of time by undergoing phase change. In further embodiments, the insulative layers 125 can be constructed substantially entirely from a PCM. In yet further embodiments, the insulative layers 125 can also include a thermally conductive area laterally offset from the semiconductor components 128, or combination of the foregoing configurations, materials, and/or structures. Examples of certain embodiments of the insulative layers 125 are described in more detail below with reference to FIGS. 3A-3C.

Figure 2B:
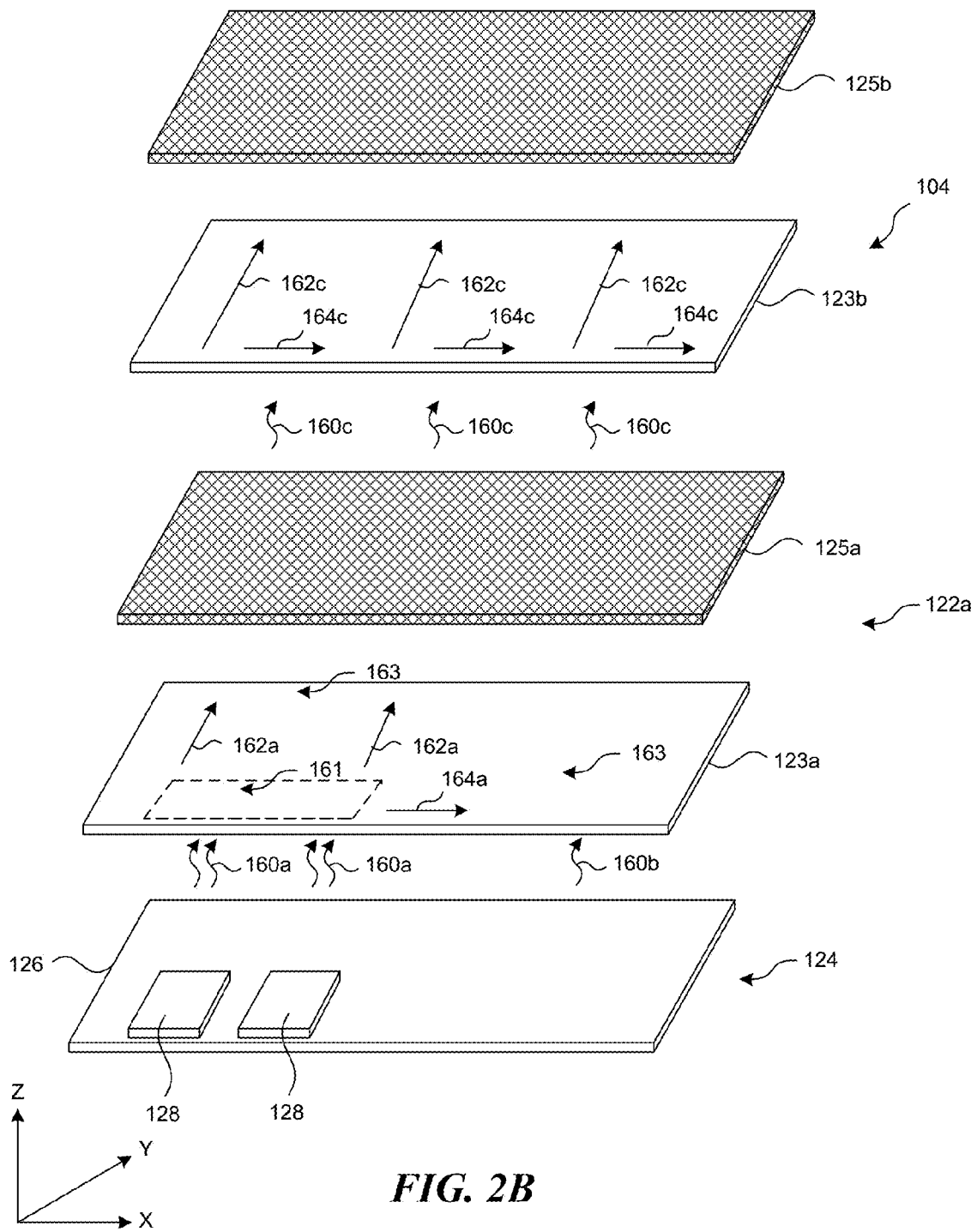
FIGS. 2B-2E are partial and exploded perspective views of the ultrasound scanner in FIG. 2A in accordance with various embodiments of the technology.

FIGS. 2B-2E are exploded perspective views of the first heat distributor 122a relative to the electronic component 124 in accordance with various embodiments of the technology. In FIGS. 2B-2E, the conductive layers 123 and the insulative layers 125 are separated from one another for purposes of clarity. As shown in FIG. 2B, the semiconductor devices 128 of the electronic component 124 can generate a large heat flux (as indicated by the double arrows 160a) while other areas of the electronic component 124 do not generate as much heat (as indicated by the single arrow 160b). This causes a high-temperature area 161 in the first conductive layer 123a of the first heat distributor 122a that is generally superimposed with the footprint of the semiconductor devices 128 or other heat generating components of the electronic component 124. Other areas of the electronic component 124 located laterally with respect to the high-temperature area 161 are relatively low-temperature areas 163. One of ordinary skill in the art will recognize that the threshold between the high-temperature and low-temperature areas 161 and 163 may be selected based on particularity of design and/or application.

In operation, the heat flux 160a at the high temperature area 161 is absorbed and distributed by the first heat distributor 122a. In the illustrated embodiment, for example, the first conductive layer 123a, the first insulative layer 125a, the second conductive layer 123b, and the second insulative layer 125b alternate between conducting and absorbing the heat to drive the heat flux laterally relative to a direction normal to the surface of the high-temperature area 161. The second insulating layer 125b also insulates the housing 120 from the heat. In other embodiments, the first heat distributor 122a may be inverted with respect to the electronic component 124 such that the foregoing heat conduction sequence is reversed. In further embodiments, the first heat distributor 122a can also have other suitable heat conduction arrangements.

Several embodiments of the first heat distributor 122a can spread out the localized heat flux 160a from the high-temperature area 161 toward low-temperature areas 163 via anisotropic heat conduction such that the risk of hot spots is at least reduced or eliminated. For example, as shown in FIG. 2B, the first conductive layer 123a conducts the heat flux 160a along the Z-axis (e.g., the axis normal to the outer surface of the semiconductor devices 128), but the first insulating layer 125a restricts heat flow along the Z-axis. As a result, the heat will preferentially flow laterally through the first conductive layer 123 faster than through the first insulating layer 125a such that the first conductive layer 123a preferentially conducts at least a portion of the heat from the high-temperature area 161 toward the low-temperature area 163 along the X- and/or Y-axis (as indicated by the arrows 162a and 164a, respectively). The first insulative layer 125a accordingly provides a thermal barrier for heat conduction farther along the Z-axis toward the second conductive layer 123b. As a result, the heat flux (as indicated by the arrows 160c) leaving the first insulative layer 125a to the second conductive layer 123b is distributed over a larger surface area than that of the high-temperature area 161.

The term "anisotropic heat conduction" used herein can thus generally refer to conducting heat from the electronic component 124 at least partially in a lateral direction with respect to the surface of the housing 120 at a first heat transfer rate and conducting heat in a direction normal to the outer surface of the electronic component 124 at a second heat transfer rate different than the first heat transfer rate. The first heat transfer rate is generally greater than the second heat transfer rate. The second conductive layer 123b and the second insulative layer 125b can further distribute the heat flux 160c in a generally similar fashion (as indicated by the arrows 162c and 164c).

Figure 2C:
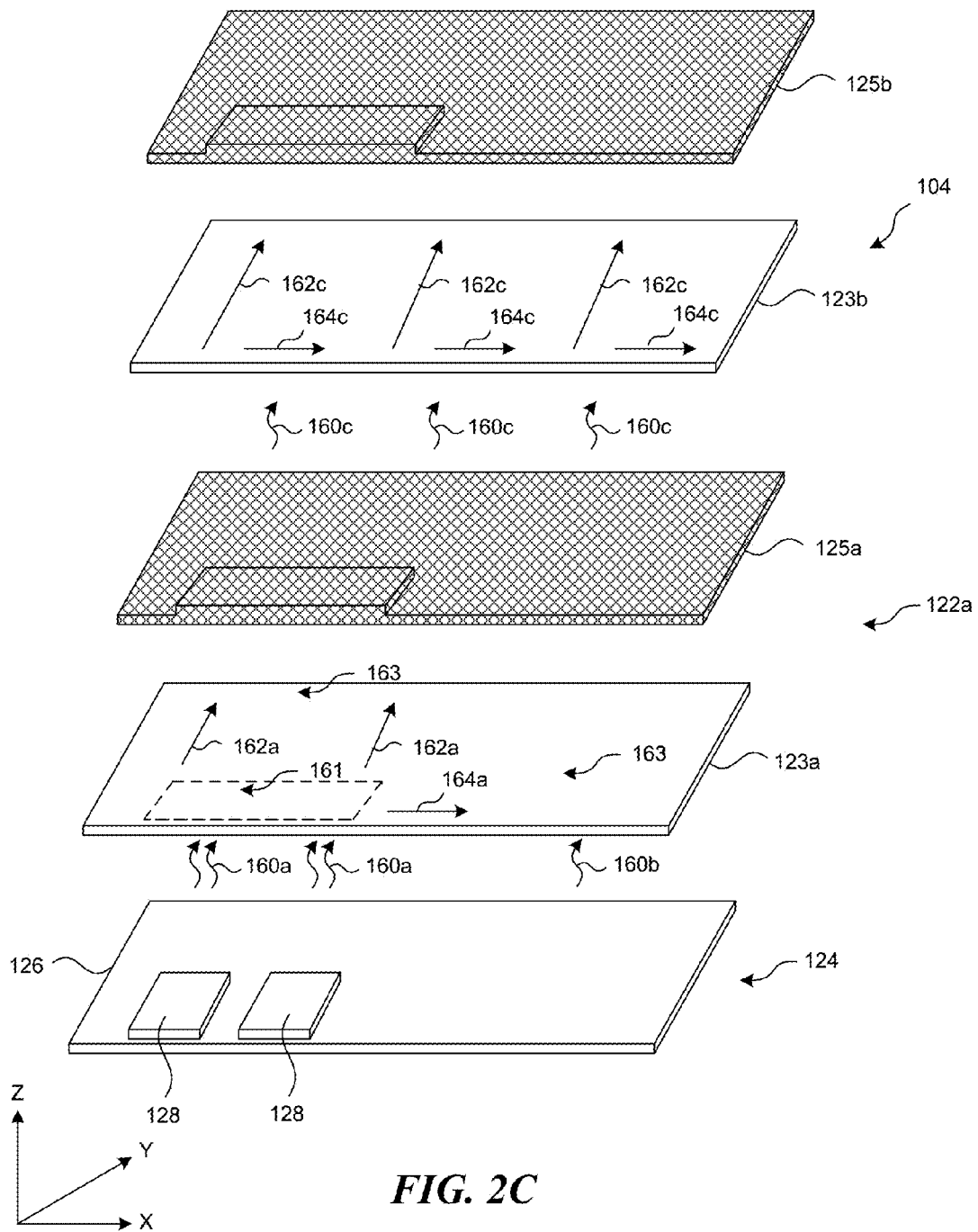
Figure 2D:
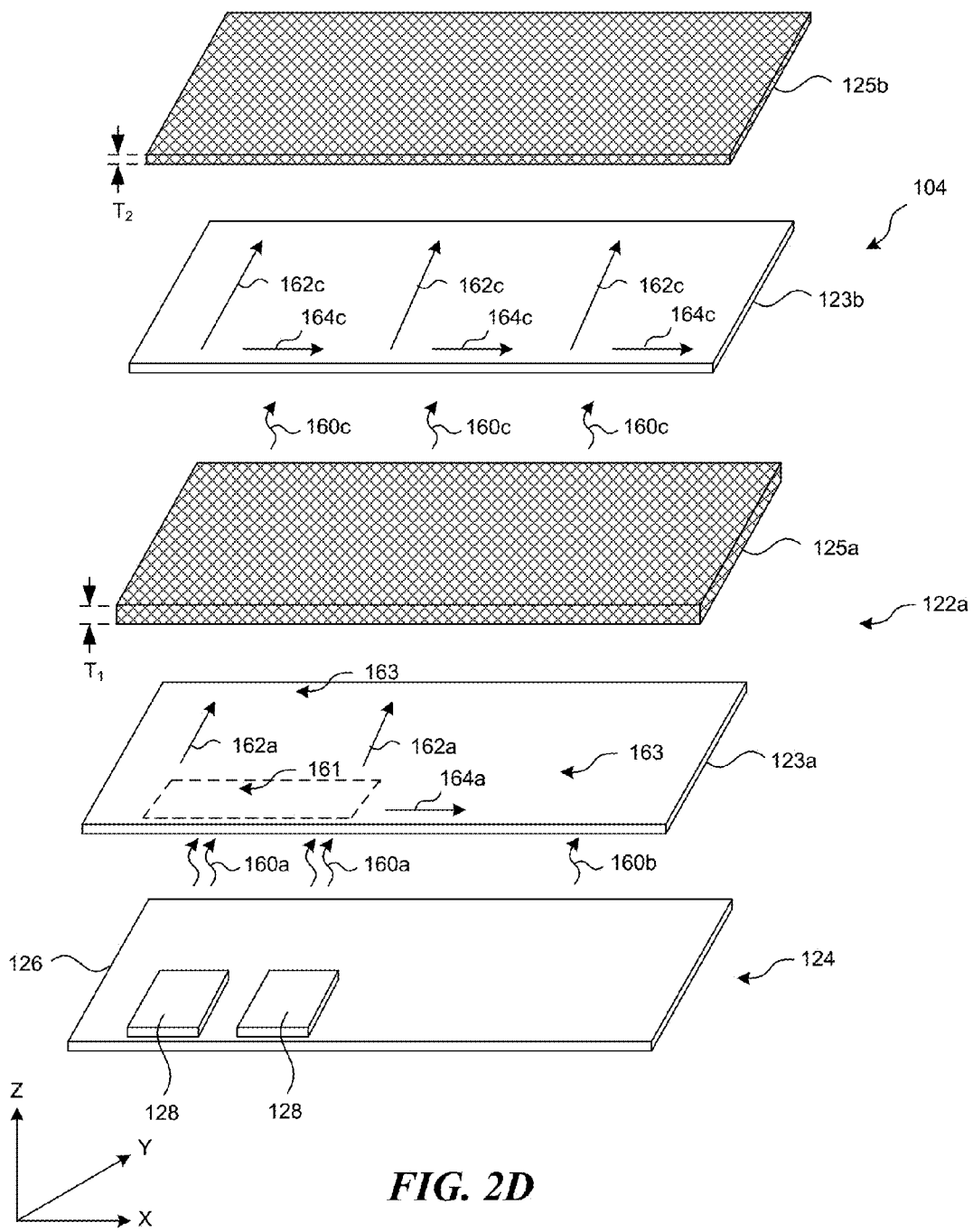

The distribution of the heat fluxes 160a, 160b and 160c can be influenced by adjusting various parameters of the first heat distributor 122a. For example, the distribution of the heat fluxes 160a and 160b can be influenced by adjusting at least one of (1) a thermal conductivity of the individual insulative layers 125, (2) a thermal conductivity of the individual conductive layers 123, (3) a thickness, a width, and/or a length of the insulative layers 125 and the conductive layers 123, and/or (4) openings and/or thermally conductive/insulative materials aligned with the hotter or cooler areas. For example, in one embodiment, the thickness of the individual insulative layers 125 can be increased from a first thickness (e.g., 2 mm) to a second thickness (e.g., 4 mm) at areas generally aligned with the semiconductor devices 128 (as shown in FIG. 2C) or across their entire area (as shown in FIG. 2D) such that the individual conductive layers 123 can spread out the heat flux farther along the X- and/or Y-axis. In other embodiments, other suitable characteristics of the first heat distributor 122a may also be adjusted to achieve a desired heat flux distribution.

Figure 2E:
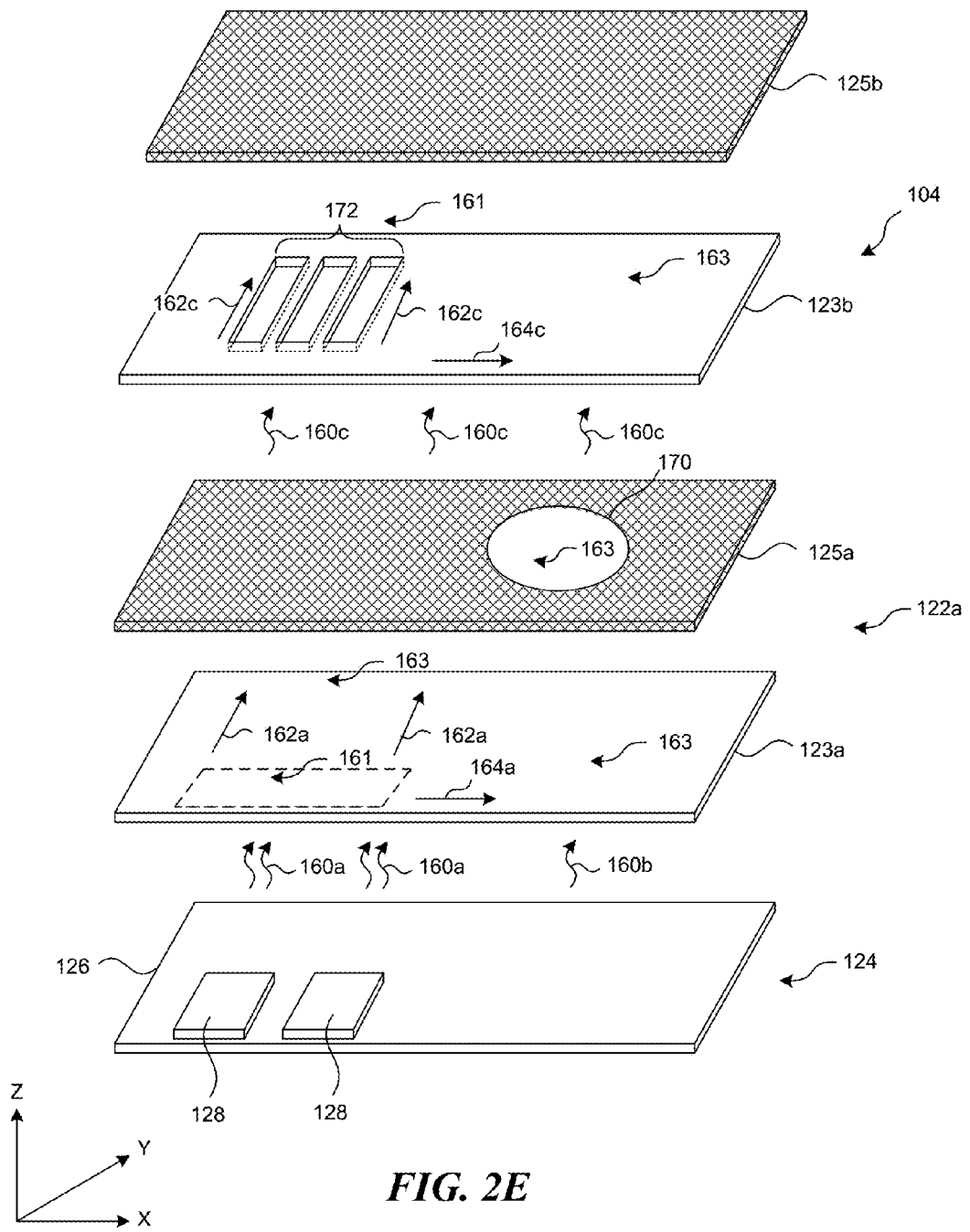

The distribution of the heat fluxes 160a, 160b and 160c can also be influenced by incorporating structural features into the conductive layers 123 and/or the insulative layers 125. For example, as shown in FIG. 2E, the first insulative layer 125a can include a more conductive region 170 in a low-temperature area 163 generally offset from the semiconductor devices 128. The conductive region 170 can allow more heat to flow from the first conductive layer 123a to the second conductive layer 123b than from other high-temperature areas of the first insulative layer 125a. As a result, more heat can flow through the low-temperature areas offset from the heat generating components (i.e., the semiconductor devices 128) to improve the distribution of heat flow. The conductive region 170 can have conductive particles or elements (e.g., metal particles) embedded in the insulating layer 125.

In another example, which may be combined with the conductive region 170 on the insulation layer 125 or stand on its own, the second conductive layer 123b can include one or more apertures, channels, slots, or openings 172 in the high-temperature area 161 generally corresponding to the semiconductor devices 128. The channels or slots 172 can reduce an amount of heat flowing through the high-temperature area 161 of the second conductive layer 123b and force more heat to flow toward and through the low-temperature area 163. In other examples, the conductive layers 123 can also include other suitable features that reduce an amount of heat flowing along the Z-axis over the hot areas while increasing the amount of heat flowing along the X- and/or Y-axis to cooler areas.

Several embodiments of the insulative layers 125 can also reduce a rate of temperature increase at the surface of the ultrasound scanner 104 due to their low thermal conductivity. In certain embodiments, the insulative layers 125 can further reduce the rate of temperature increase at the surface of the ultrasound scanner 104 by incorporating a PCM. For example, the first insulative layer 125a can absorb a portion of the heat flux 160a with a PCM embedded or otherwise distributed in a foam or other matrix having a low thermal conductivity. As a result, the heat flux 160b reaching the second conductive layer 123b can be less than the heat flux 160a at the first conductive layer 123a. More specifically, the second insulative layer 125b can maintain a relatively constant temperature while absorbing the heat fluxes 160a and 160b as the PCM changes phase. The phase change of the PCM temporarily reduces the heat flux flowing toward the surface of the housing 120 to allow the conductive layers 123 to distribute more of the heat laterally. The reduced heat flux to the surface of the housing superimposed with the semiconductor components 128 can also result in a low rate of temperature increase at these areas of the surface of the ultrasound scanner 104 during an initial period of operation.

Figure 3A:
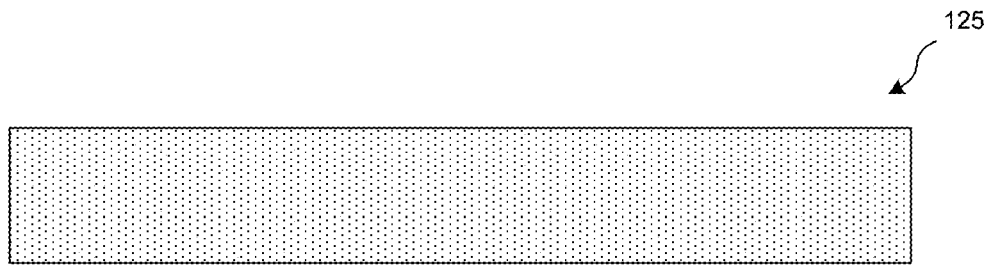
FIGS. 3A-3C are cross-sectional views of an insulative layer suitable for use in the ultrasound scanner in FIG. 2A in accordance with embodiments of the technology.
Figure 3B:
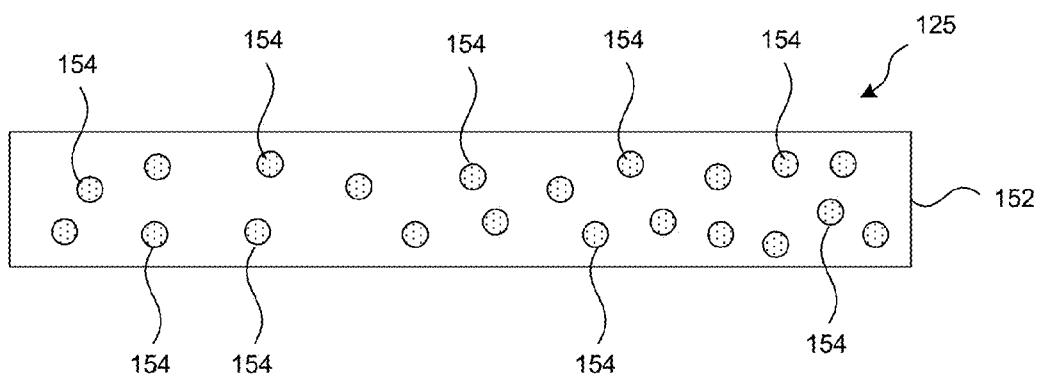
Figure 3C:
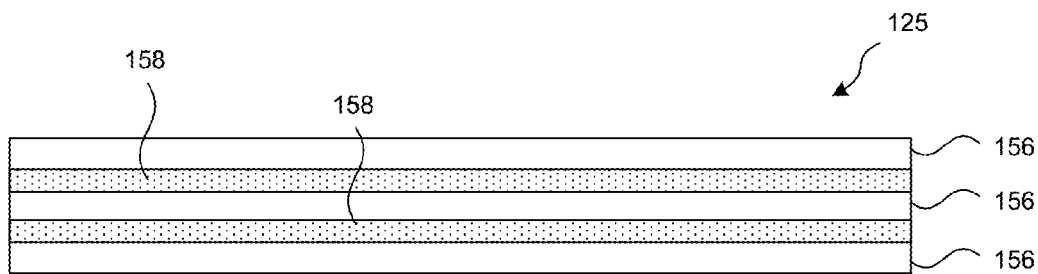

FIGS. 3A-3C are cross-sectional views of one of the insulative layers 125 suitable for use in the ultrasound scanner in FIG. 2A in accordance with embodiments of the technology. As shown in FIG. 3A, one embodiment of the insulative layer 125 can include a solid slab of a PCM. One suitable PCM is a phase change material (Model No. MPCM37-D) provided by Microtek Laboratories, Inc. of Dayton Ohio. In other embodiments, the insulative layer 125 can also include a solid slab of other suitable insulating material. As shown in FIG. 3B, another embodiment of the insulative layer 125 can include a substrate 152 (e.g., an epoxy) or other type of insulative matrix and one or more phase change structures 154 embedded or otherwise distributed in the substrate 152.

In the illustrated embodiment, the phase change structures 154 are a plurality of spheres distributed generally randomly throughout the substrate 152. In other embodiments, the phase change structures 154 can also include a plurality of cubes, hemispheres, and/or other suitable structures arranged as an array and/or having other suitable arrangements. As shown in FIG. 3C, another embodiment of the insulative layer 125 can include a plurality of insulative strata 156 (e.g., epoxy layers) alternately laminated with a plurality of phase change strata 158.

Figure 4A:
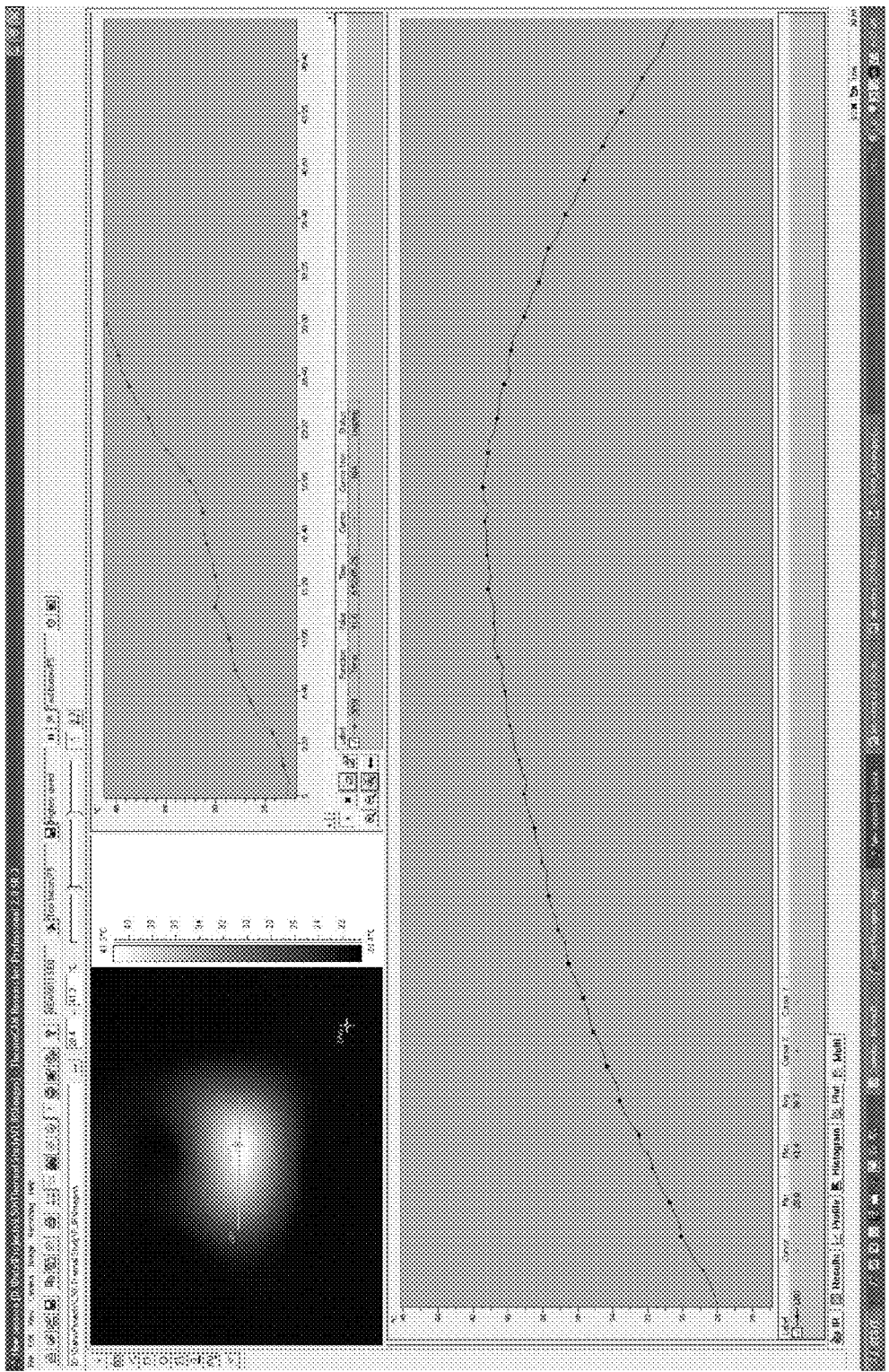
FIGS. 4A-4E are screen prints illustrating experimental results of an ultrasound scanner with anisotropic heat distributors in accordance with embodiments of the technology.
Figure 4B:
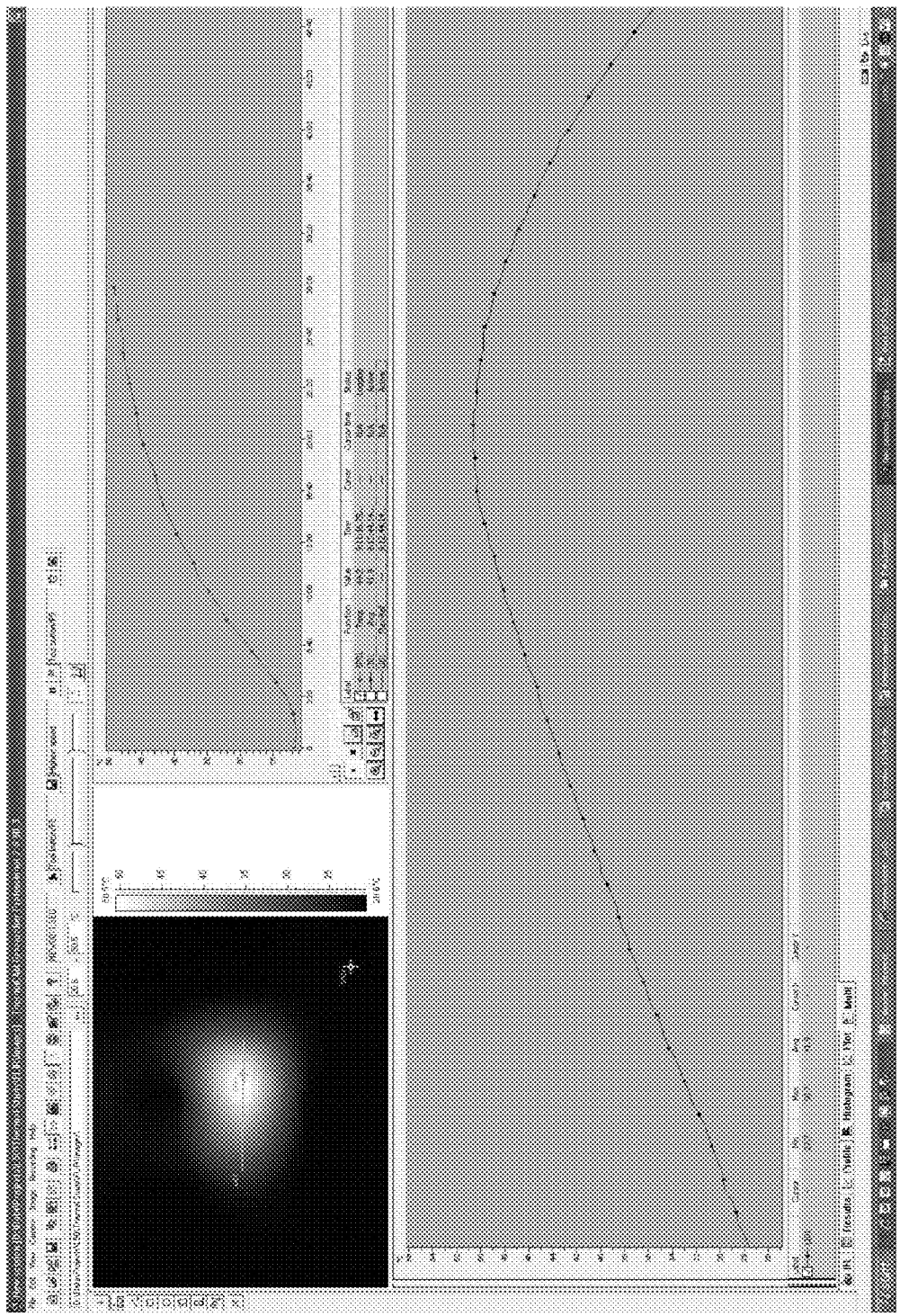
Figure 4C:
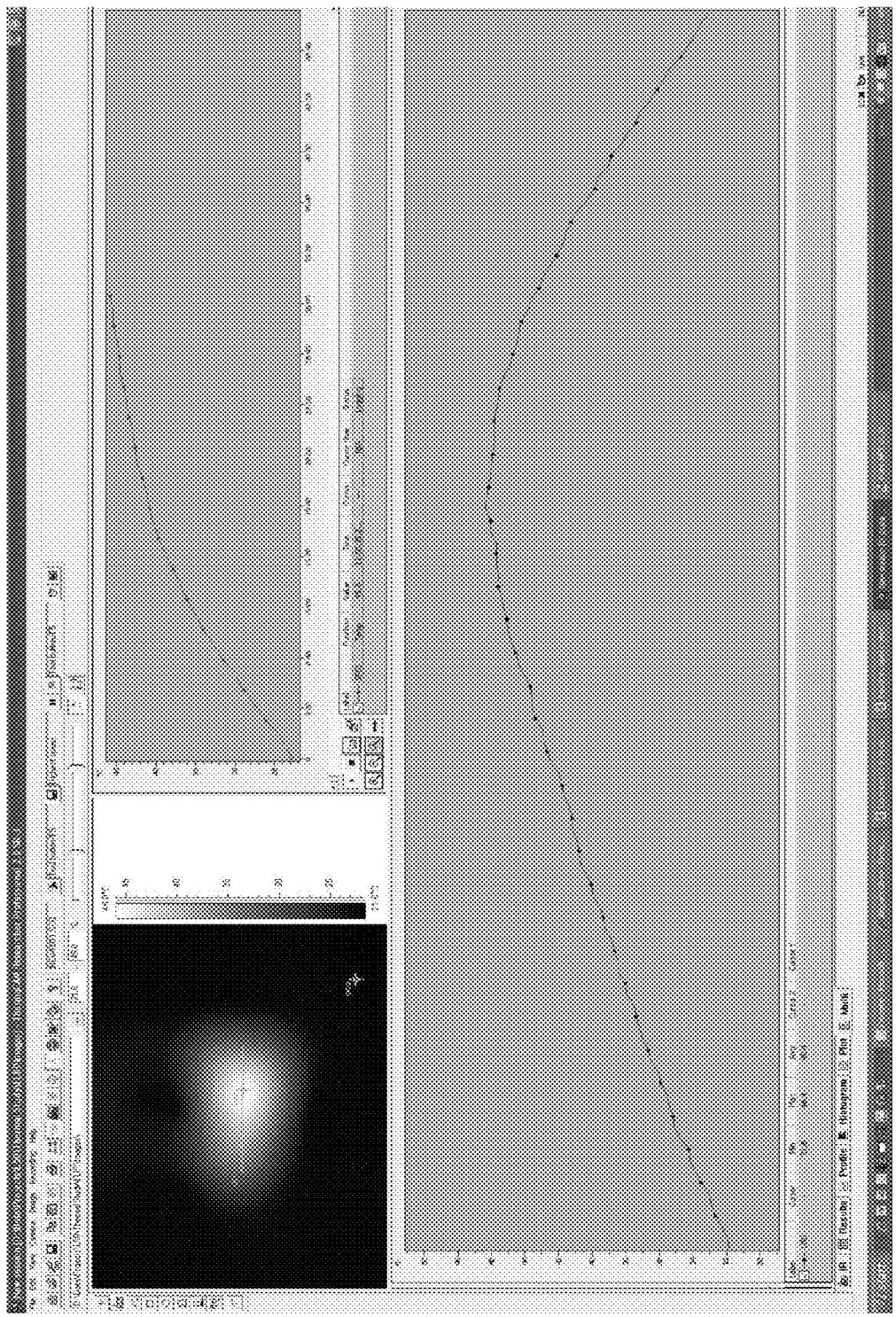
Figure 4D:
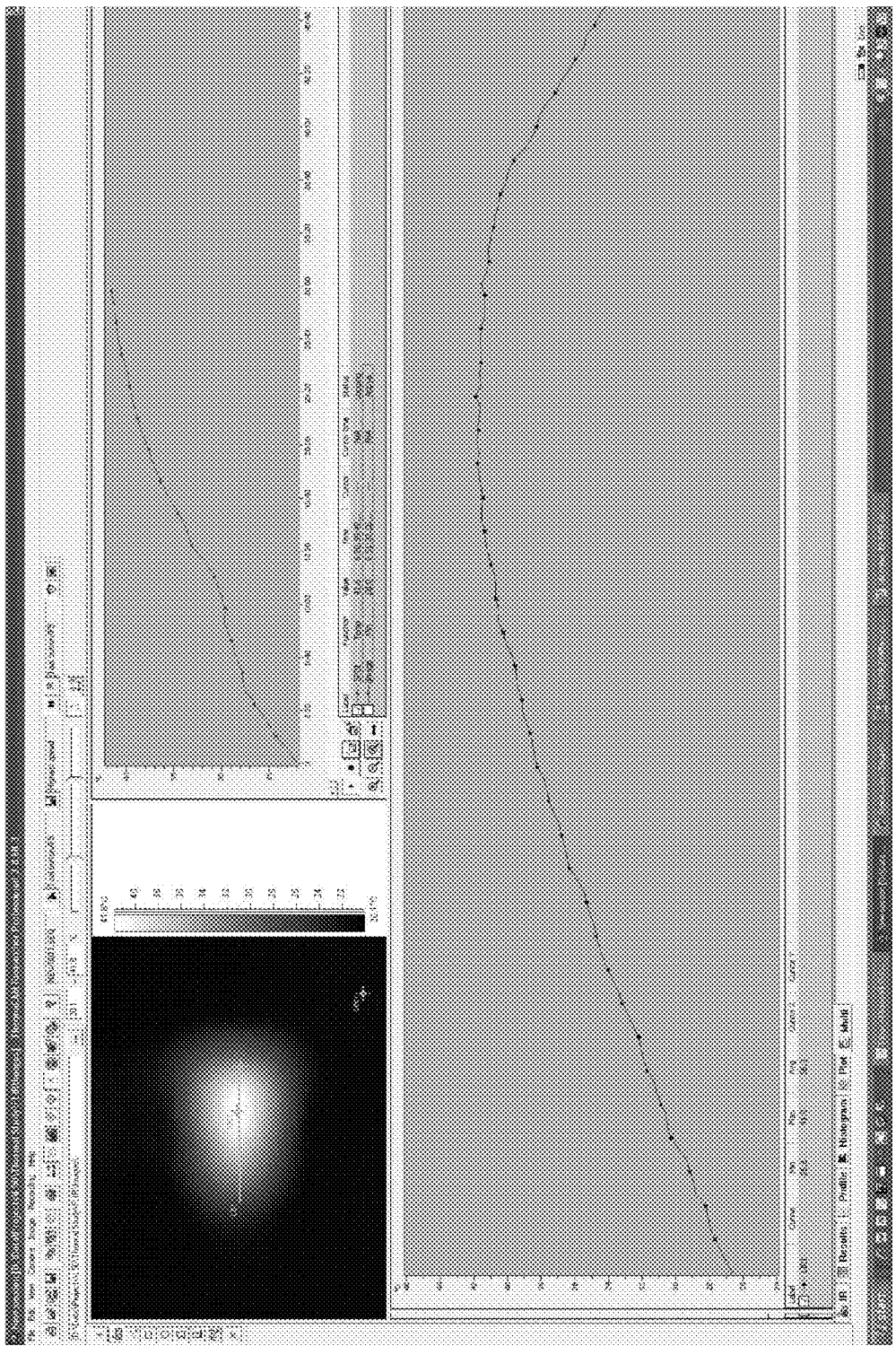
Figure 4E:
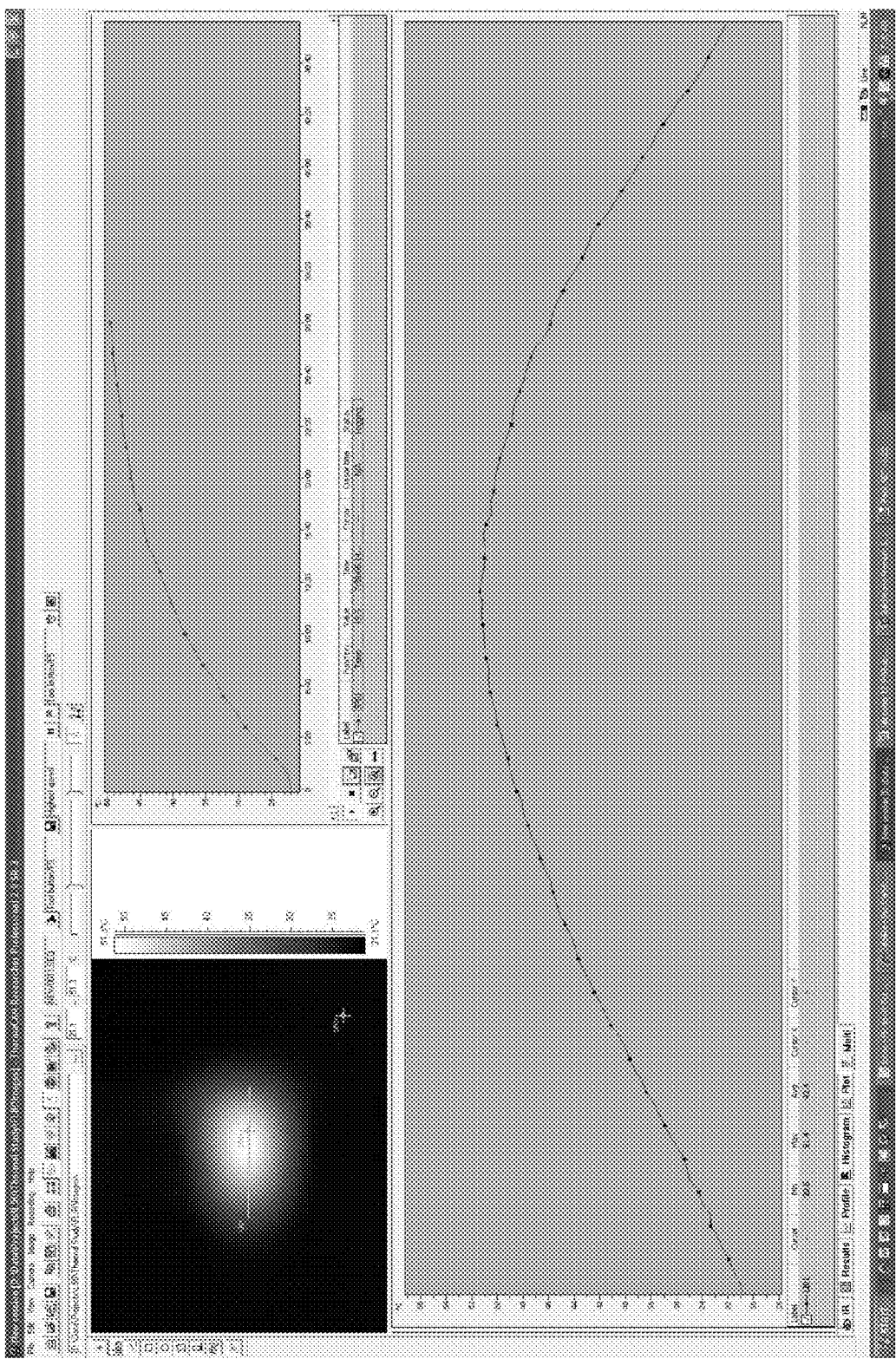

Tests were conducted to examine an ultrasound scanner with a heat distributor generally similar to several embodiments of the first heat distributor 122a in FIG. 2A. The test results are shown in FIGS. 4A-4E as (1) a color plot of temperature profile (upper left), (2) a temperature versus time chart (upper right), and (3) a temperature versus location chart (lower). In a first test, a heat distributor with two copper foils separated by a slab of a PCM (approximately 0.2" thick, Model No. MPCM37-D provided by Microtek Laboratories, Inc. of Dayton Ohio) was used. The result of the first test is shown in FIG. 4A. In a second test, a heat distributor with only one copper foil (approximately 0.026" thick) was used. The result of the second test is shown in FIG. 4B. In a third test, a heat distributor with five layers of copper foils separated from one another by a layer of cotton gauze was used. The result of the third test is shown in FIG. 4C. In a fourth test, a heat distributor with four layers of copper foils separated by three layers of cotton gauze impregnated with a PCM were used. The result of the fourth test is shown in FIG. 4D. As a comparison, in a fifth test, no heat distributor was used. The result of the fifth test is shown in FIG. 4E. As clearly shown in FIGS. 4A-4E, utilizing embodiments of the heat distributor can more evenly distribute heat across the surface of the housing, and can lower the rate of temperature increase at the surface of the housing.

From the foregoing, it will be appreciated that specific embodiments of the technology have been described herein for purposes of illustration, but that various modifications may be made without deviating from the disclosure. Many of the elements of one embodiment may be combined with other embodiments in addition to or in lieu of the elements of the other embodiments. Accordingly, the disclosure is not limited except as by the appended claims.

We claim:

1. An ultrasound scanner, comprising:
an ultrasound probe with a housing having a surface enclosing an internal cavity;
a printed circuit board (PCB) in the internal cavity of the housing that includes a plurality of semiconductor devices carried by the printed circuit board (PCB); and
a heat distributor between the surface of the housing and the printed circuit board, the heat distributor being in thermal communication with both the semiconductor devices and the surface of the housing, wherein the heat distributor includes a laminated structure having at least two conductive layers including at least a first conductive layer that is thermally coupled to at least one heat producing semiconductor device, a second conductive layer that is thermally coupled to the surface of the housing and an insulative layer disposed between the first and second conductive layers, wherein the insulative layer includes a region that is more heat conductive than a surrounding region of the insulative layer and that is laterally offset from the heat producing semiconductor device to allow heat to flow from the first conductive layer to the second conductive layer of the laminated structure.

2. The ultrasound scanner of claim 1 wherein:
the second conductive layer includes an opening in an area superimposed with the heat producing semiconductor device on the PCB.

3. The ultrasound scanner of claim 1 wherein;
the heat distributor includes a third conductive layer separated from the second conductive layer by a second insulative layer;
wherein the first, second and third conductive layers have a thermal conductivity greater than 10 W/(m·K); and
the first and second insulative layers have a thermal conductivity less than 10 W/(m·K).

4. The ultrasound scanner of claim 1 wherein:
the heat distributor includes a third conductive layer separated from the second conductive layer by a second insulative layer; and
wherein at least one of the first and second insulative layers includes a phase change material configured to undergo a phase change upon absorption of heat.

5. The ultrasound scanner of claim 1 wherein:
the heat distributor includes a third conductive layer separated from the second conductive layer by a second insulative layer; and
wherein the first and second insulative layers include a sheet of a phase change material configured to undergo a phase change upon absorption of heat.

6. The ultrasound scanner of claim 1 wherein:
the first and second conductive layers are separated from one another by a plurality of insulative layers; and
the plurality of insulative layers include a substrate and a phase change material embedded in the substrate, the phase change material being configured to undergo a phase change upon absorption of heat.

7. The ultrasound scanner of claim wherein:
the second conductive layer includes an opening in an area corresponding to the heat producing semiconductor device on the PCB.

8. The ultrasound scanner of claim 1, wherein the insulative layer includes a phase change material.

9. An ultrasound scanner, comprising:
an ultrasound probe with housing having a surface and a wall enclosing an internal cavity;
an electronic component in the internal cavity of the housing, the electronic component having a printed circuit board (PCB) that supports one or more semiconductor devices with an outer surface; and
a heat distributor between the surface of the housing and the electronic component, the heat distributor including at least two conductive layers to conduct heat from heat producing semiconductor device at least partially in a lateral direction with respect to the surface of the housing at a first heat transfer rate and an insulative layer positioned between the two conductive layers to conduct heat in a direction normal to the outer surface of the heat producing semiconductor device at a second heat transfer rate different than the first heat transfer rate, wherein the insulative layer includes a region that is laterally offset from the heat producing semiconductor device and is more heat conductive than a surrounding region of the insulative layer to conduct heat from a first conductive layer to a second conductive layer of the two conductive layers.

10. The ultrasound scanner of claim 9 wherein the insulative layer includes a phase change material configured to undergo a phase change upon absorption of heat.

11. The ultrasound scanner of claim 9 wherein:
the electronic component includes a high-temperature area and a lower-temperature area of the printed circuit board;
wherein the second conductive layer is adjacent the surface of the housing and includes an opening in an area corresponding to the high-temperature area of the PCB.

12. The ultrasound scanner of claim 9 wherein;
the electronic component includes a high-temperature area and a lower-temperature area of the printed circuit board;
wherein the second conductive layer is adjacent the surface of the housing and includes an opening in an area corresponding to the high-temperature area of the PCB;
and wherein the insulative layer includes a phase change material configured to undergo a phase change upon absorption of heat.

13. The ultrasound scanner of claim 9 wherein:
the electronic component includes a high-temperature area and a lower-temperature area;
and wherein at least one of the two conductive layers includes a copper foil; and
the insulative layer includes a cotton gauze.

* * * * *

UNITED STATES PATENT AND TRADEMARK OFFICE
CERTIFICATE OF CORRECTION

Page 1 of 1

PATENT NO. : 9,186,123 B1
APPLICATION NO. : 12/862618
DATED : November 17, 2015
INVENTOR(S) : Paul Dunham, Dustin Green and Thomas Houck It is certified that error appears in the above-identified patent and that said Letters Patent is hereby corrected as shown below:

In the Claims

In Claim 7, Column 9, Line 35, the line should read "The ultrasound scanner of claim 1 wherein:"

Signed and Sealed this
Fifteenth Day of December, 2020

Andrei Iancu
*Director of the United States Patent and Trademark Office*